US012570752B2

(12) United States Patent
Biswas et al.

(10) Patent No.: US 12,570,752 B2
(45) Date of Patent: Mar. 10, 2026

(54) COMBINATION THERAPY WITH AN ANTI BCMA ANTIBODY AND A GAMMA SECRETASE INHIBITOR

(71) Applicant: SPRINGWORKS THERAPEUTICS, INC., Stamford, CT (US)

(72) Inventors: Swethajit Biswas, Uxbridge (GB); Beata Holkova, Collegeville, PA (US); Katarina Luptakova, Waltham, MA (US)

(73) Assignee: SPRINGWORKS THERAPEUTICS, INC., Stamford, CT (US)

( * ) Notice: Subject to any disclaimer, the term of this patent is extended or adjusted under 35 U.S.C. 154(b) by 1098 days.

(21) Appl. No.: 17/602,434

(22) PCT Filed: Apr. 9, 2020

(86) PCT No.: PCT/IB2020/053397
§ 371 (c)(1),
(2) Date: Oct. 8, 2021

(87) PCT Pub. No.: WO2020/208572
PCT Pub. Date: Oct. 15, 2020

(65) Prior Publication Data

US 2022/0168417 A1 Jun. 2, 2022

Related U.S. Application Data

(60) Provisional application No. 62/943,480, filed on Dec. 4, 2019, provisional application No. 62/831,913, filed on Apr. 10, 2019.

(51) Int. Cl.
*C07K 16/28* (2006.01)
*A61K 31/417* (2006.01)
(Continued)

(52) U.S. Cl.
CPC ........ *C07K 16/2878* (2013.01); *A61K 31/417* (2013.01); *A61K 39/3955* (2013.01);
(Continued)

(58) Field of Classification Search
CPC ............ C07K 16/2878; C07K 2317/00; C07K 2317/76; C07K 2317/565; A61K 31/417;
(Continued)

(56) References Cited

U.S. PATENT DOCUMENTS 11,353,458 B2 * 6/2022 Bounds .............. C07K 16/2878
11,872,211 B2 * 1/2024 Lim ........................ A61P 35/00
(Continued)

FOREIGN PATENT DOCUMENTS

WO WO 2017/093942 A1 6/2017
WO WO 2018/201051 A1 11/2018

OTHER PUBLICATIONS

Tai et al. Novel anti-B-cell maturation antigen antibody-drug conjugate (GSK2857916) selectively induces killing of multiple myeloma. Blood. May 15, 2014;123(20):3128-38. doi: 10.1182/blood-2013-10-535088. Epub Feb. 25, 2014. PMID: 24569262; PMCID: PMC4023420. (Year: 2014).*
(Continued)

*Primary Examiner* — Mark Halvorson
*Assistant Examiner* — Lea S O'Brien
(74) *Attorney, Agent, or Firm* — Blank Rome LLP

(57) ABSTRACT

The disclosure concerns a method of treating cancer, especially, such as multiple myeloma, involving the combination of an anti-BCMA (B cell maturation antigen) antibody, Belantamab mafodotin -GSK2857916- and a gamma-secretase inhibitor, e.g., nirogacestat -PF03084014-. The disclosure also relates to dosages, duration of treatment and
(Continued)

Figure 1:
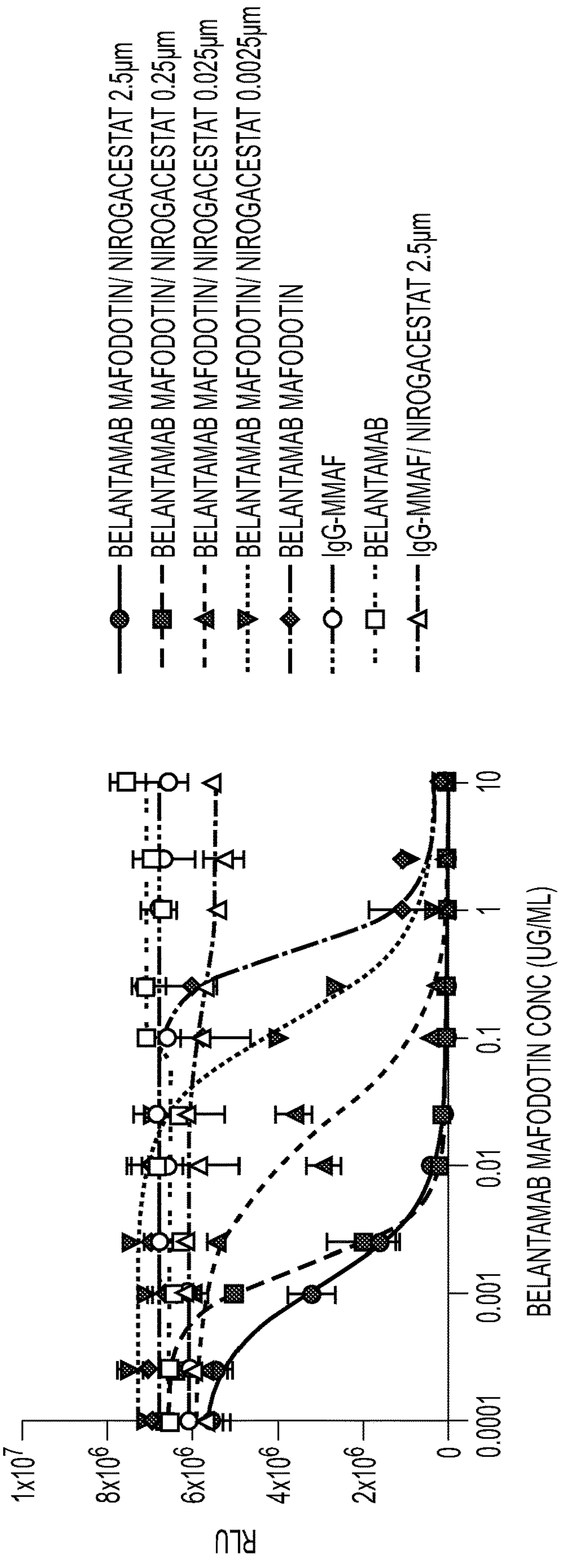

time lapses between administration of the anti-BCMA antibody and the gamma-secretase inhibitor.

17 Claims, 6 Drawing Sheets

Specification includes a Sequence Listing.

(51) Int. Cl.

| | |
|---|---|
| ***A61K 39/00*** | (2006.01) |
| ***A61K 39/395*** | (2006.01) |
| ***A61K 47/68*** | (2017.01) |
| ***A61P 35/00*** | (2006.01) |
| ***A61P 35/02*** | (2006.01) |

(52) U.S. Cl.
CPC .... *A61K 47/68031* (2023.08); *A61K 47/6849* (2017.08); *A61P 35/00* (2018.01); *A61P 35/02* (2018.01); *A61K 39/395* (2013.01); *A61K 2039/505* (2013.01); *A61K 2039/545* (2013.01); *A61K 2300/00* (2013.01); *C07K 2317/00* (2013.01); *C07K 2317/565* (2013.01); *C07K 2317/76* (2013.01)

(58) Field of Classification Search
CPC .......... A61K 39/3955; A61K 47/68031; A61K 2039/505; A61K 47/6849; A61K 39/395; A61K 2039/545; A61K 2300/00; A61P 35/00; A61P 35/02
See application file for complete search history.

(56) References Cited

U.S. PATENT DOCUMENTS

| | | | | |
|---|---|---|---|---|
| 11,925,619 | B2 * | 3/2024 | Lim | A61K 31/4164 |
| 11,925,620 | B1 * | 3/2024 | Lim | A61K 31/4164 |
| 11,938,116 | B2 * | 3/2024 | Lim | A61P 35/00 |
| 11,951,096 | B2 * | 4/2024 | Lim | A61P 19/00 |
| 11,957,662 | B2 * | 4/2024 | Lim | A61P 35/00 |
| 12,011,434 | B2 * | 6/2024 | Lim | A61K 31/4164 |
| 12,011,435 | B2 * | 6/2024 | Lim | A61P 19/00 |
| 12,036,207 | B2 * | 7/2024 | Lim | A61P 35/00 |
| 12,138,246 | B2 * | 11/2024 | Lim | A61K 9/0053 |

OTHER PUBLICATIONS

Kummar, Shivaani et al. "Clinical Activity of the γ-Secretase Inhibitor PF-03084014 in Adults With Desmoid Tumors (Aggressive Fibromatosis)." Journal of clinical oncology : official journal of the American Society of Clinical Oncology vol. 35,14 (2017): 1561-1569. doi:10.1200/JCO.2016.71.1994 (Year: 2017).*

Cho et al., "Targeting B Cell Maturation Antigen (BCMA) in Multiple Myeloma: Potential Uses of BCMA-Based Immunotherapy", *Frontiers in Immunology*, vol. 9, 15 pages (2018).

* cited by examiner

COMBINATION THERAPY WITH AN ANTI BCMA ANTIBODY AND A GAMMA SECRETASE INHIBITOR

This application is a 371 of International Application No. PCT/IB2020/053397 filed 9 Apr. 2020, which claims the benefit of U.S. Provisional Application No. 62/831,913 filed 10 Apr. 2019, and U.S. Provisional Application No. 62/943,480 filed 4 Dec. 2019 the disclosures of which are incorporated herein in their entireties.

FIELD OF THE INVENTION

The present invention relates to combination therapy of a pharmaceutically active antigen binding protein, for example a monoclonal antibody and a gamma-secretase inhibitor for use in treating cancer. Particular dosage regimens and methods of administration are also included.

BACKGROUND TO THE INVENTION

Multiple myeloma (MM) is an incurable malignancy and accounts for 1% of all cancers and for 10% of all hematologic malignancies. A variety of drugs and combination treatments have been evaluated and found effective in treating multiple myeloma (National Comprehensive Cancer Network, 2016; Moreau, San Miguel et al., 2017). However, most, if not all, of these patients inevitably relapse (Richardson, Barlogie et al., 2003; Richardson, Barlogie et al., 2006; Jagannath, Barlogie et al., 2008).

Drug combinations are emerging for patients with previously treated MM but these regimens may be limited by toxic effects (National Comprehensive Cancer Network, 2016). Agents with new mechanisms of action that can be combined with existing therapies without an increase in serious toxicity are needed.

Low B-cell maturation antigen (BCMA) surface expression on the cancer cells or soluble BCMA can limit and prevent the efficacy of therapeutic agents due to inadequate binding to the BCMA present on the surface of the tumor cells. Low levels of other target molecules on tumor cells (e.g., CD19, CD20) that are targeted with antibody, antibody drug conjugates or chimeric antigen receptor T cells has been shown to limit the efficacy of these therapies, and enable cancer cells that express low levels of the target molecule to escape elimination. In the case of BCMA, the short extracellular portion of the molecule is cleaved from the cell surface and shed through the action of gamma-secretase (γ-secretase), a membrane-localized cellular enzyme involved in protein cleavage. This cleavage lowers the density of BCMA on cells such as myeloma cancer cells that express the molecule and results in elevated levels of soluble BCMA (sBCMA) in the serum of patients with certain autoimmune diseases (e.g., systemic lupus erythomatosis) and cancer (e.g., multiple myeloma).

Currently, there remains a need in the immunotherapy field for alternative or improved compositions and methods for more efficiently treating autoimmune disease and cancer.

SUMMARY OF THE INVENTION

In one aspect of the invention, there is provided a combination comprising an anti-BCMA antigen binding protein and a gamma-secretase inhibitor.

In another aspect of the invention, the combination comprises belantamab mafodotin and nirogacestat.

In one aspect of the present invention there is herein provided a combination comprising an anti-BCMA antigen binding protein and a gamma-secretase inhibitor for use in treating cancer.

In another aspect of the present invention there is herein provided a method of treating cancer in a subject in need thereof comprising administering a therapeutically effective dose of an anti-BCMA antigen binding protein and a gamma-secretase inhibitor.

In another aspect of the present invention as herein provided there is a kit for use in treating cancer comprising:

(i) an anti-BCMA antigen binding protein; and (ii) instructions for use when combined with a gamma-secretase inhibitor.

DESCRIPTION OF DRAWINGS/FIGURES

FIG. 1 demonstrates viability of the myeloma cell line L363 when treated with different doses of a gamma-secretase inhibitor (nirogacestat) in combination with belantamab mafodotin or control IgG-MMAF.

Figure 2:
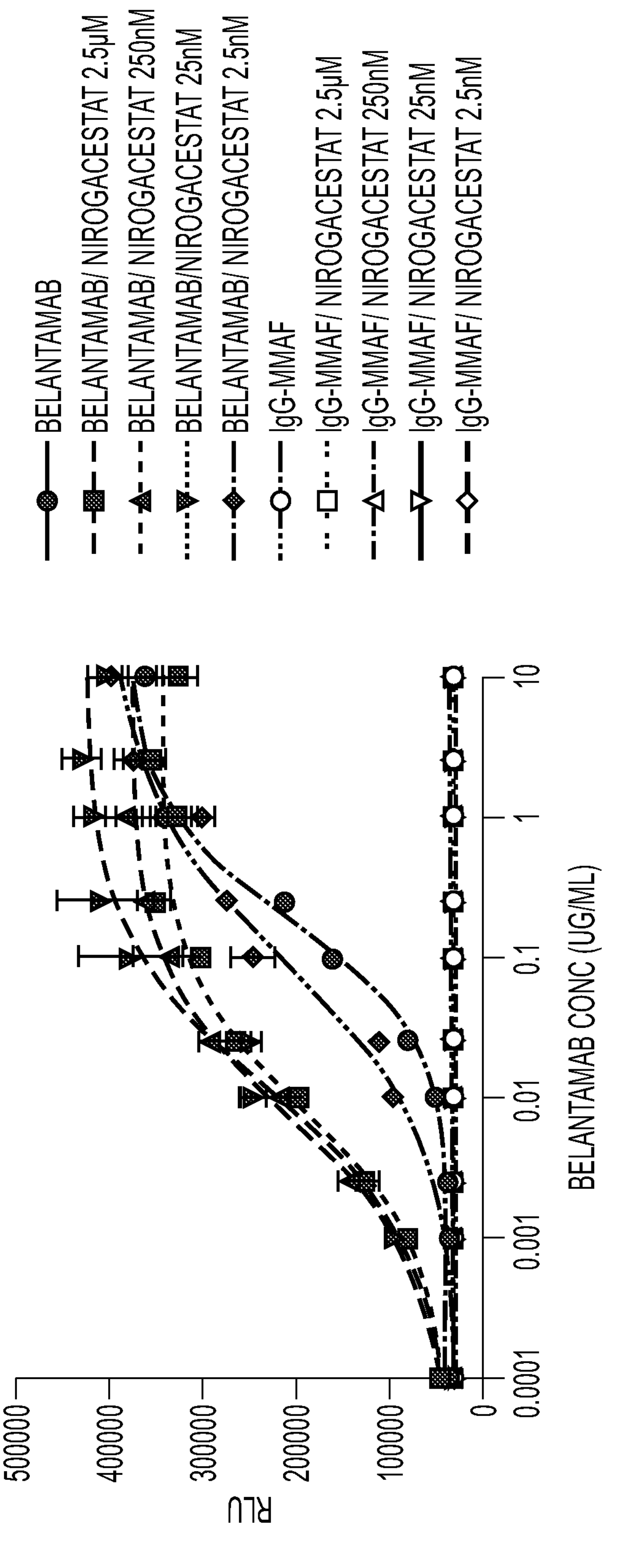

FIG. 2 demonstrates ADCC activity of belantamab mafodotin in combination with nirogacestat was evaluated in myeloma cell line L363.

Figure 3:
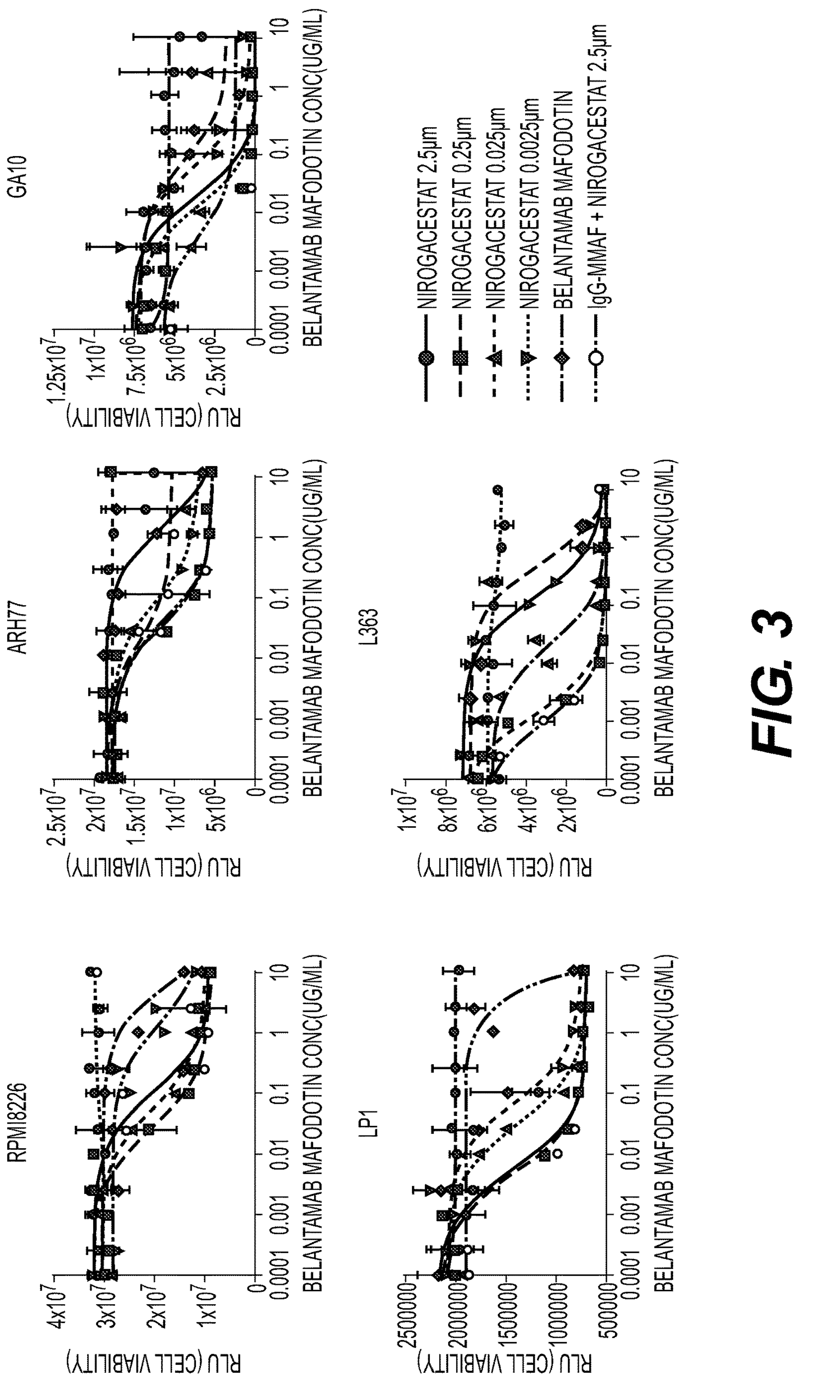

FIG. 3 demonstrates ADC Activity in BCMA-expressing cell lines.

Figure 4:
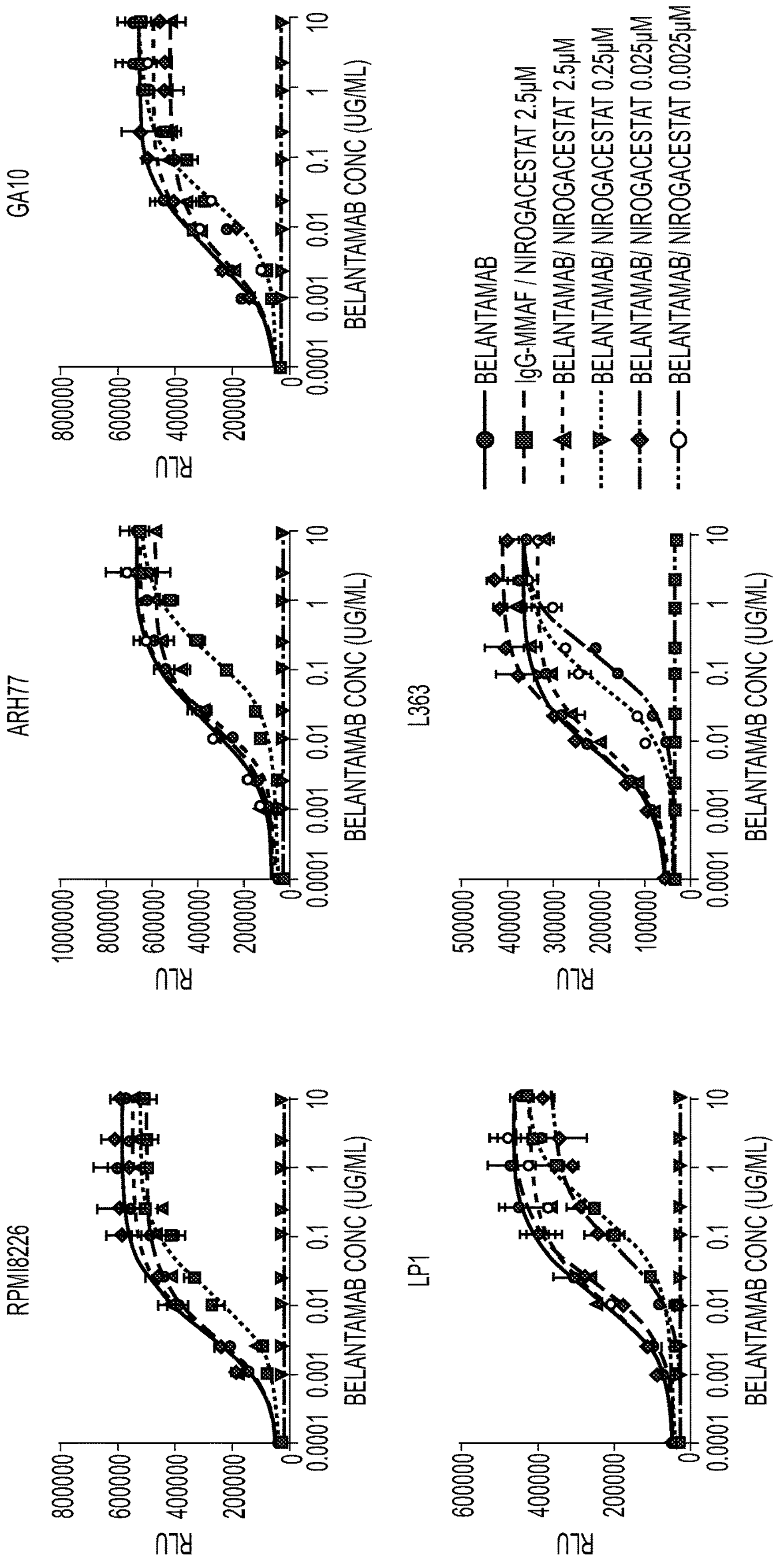

FIG. 4 demonstrates ADCC activity in BCMA expressing cell lines.

Figure 5:
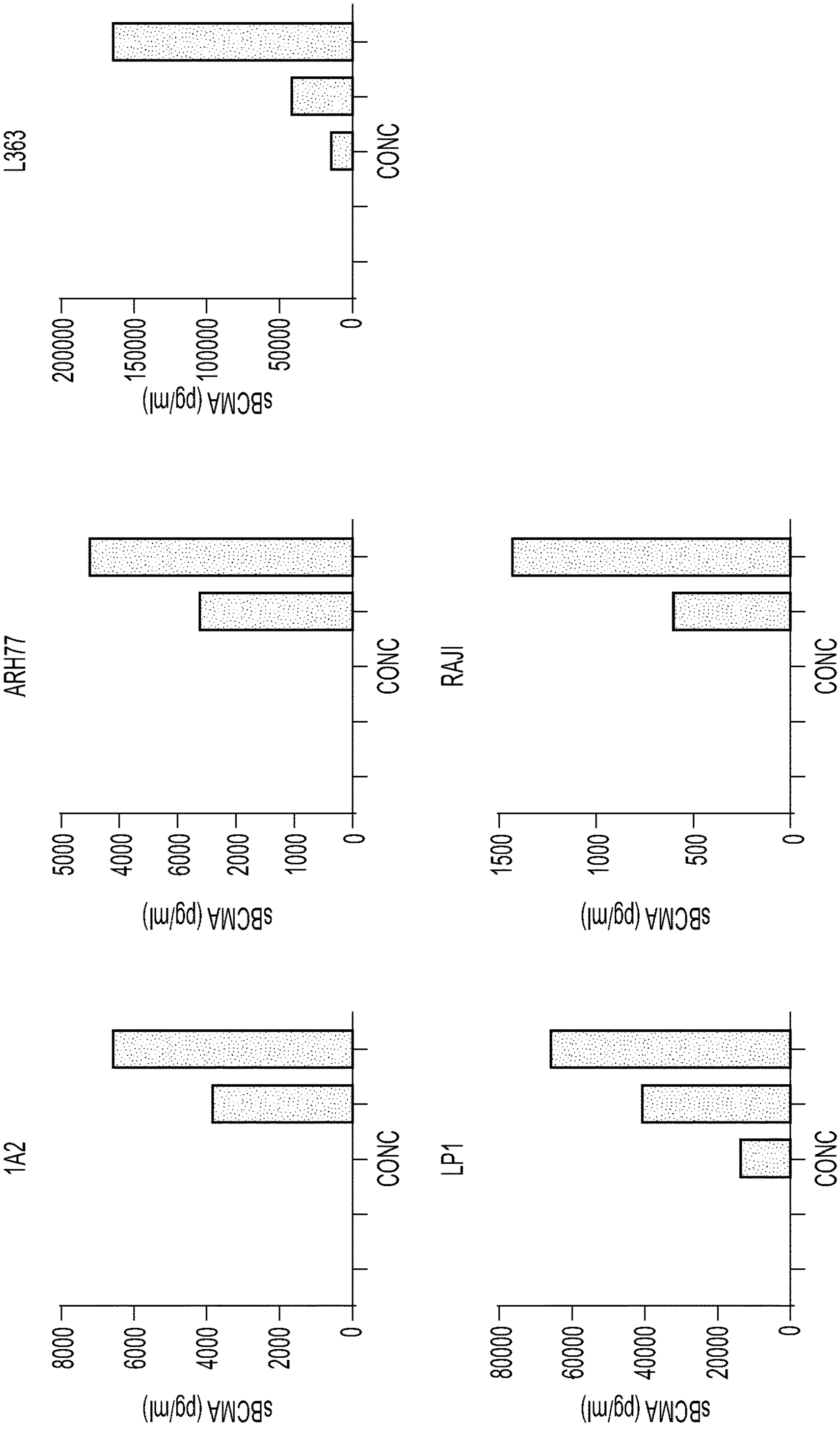

FIG. 5 demonstrates sBCMA levels following treatment with nirogacestat.

Figure 6:
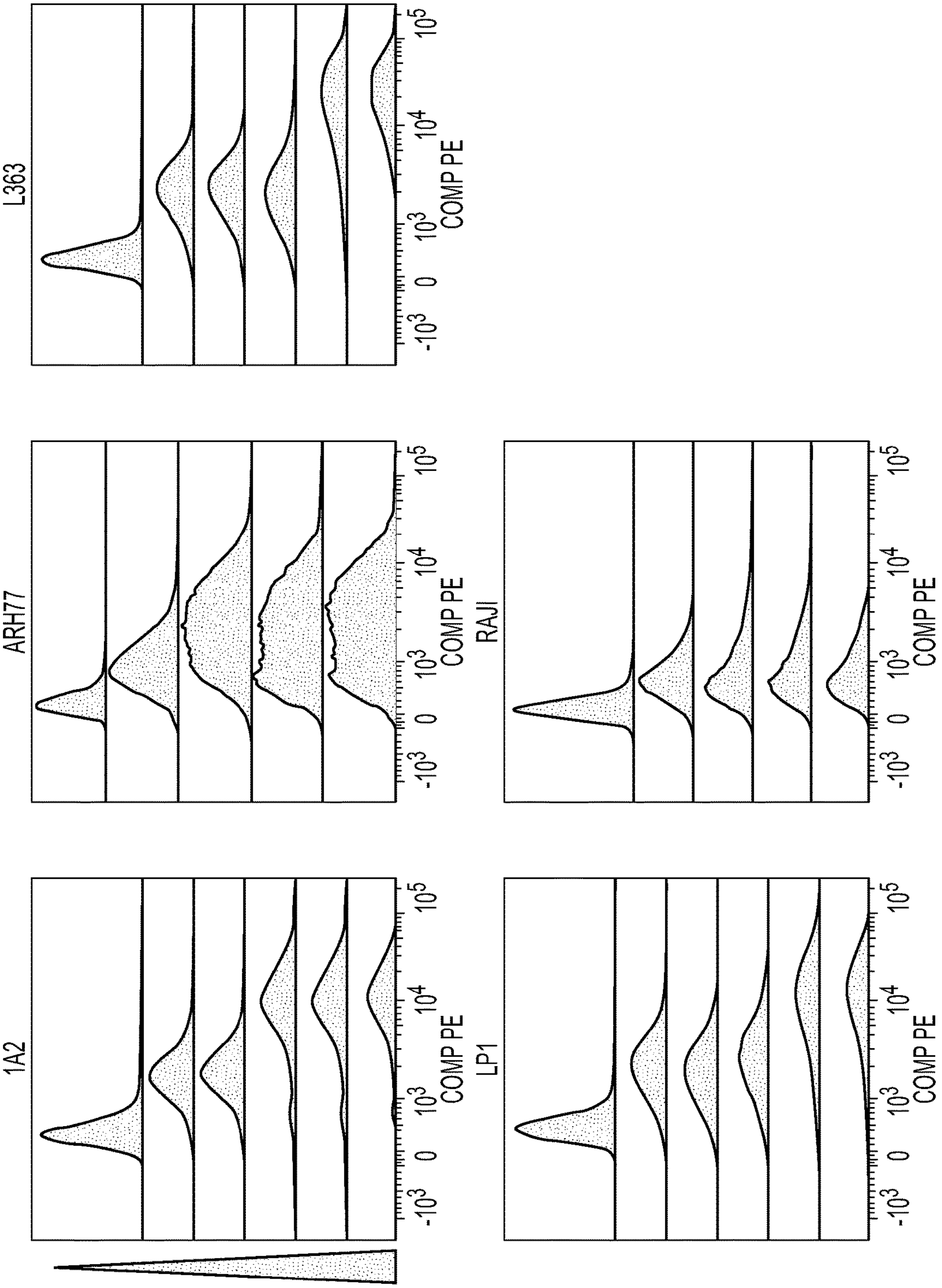

FIG. 6 demonstrates Cell surfaces levels of BCMA following treatment with nirogacestat.

DETAILED DESCRIPTION OF THE INVENTION

In one aspect of the present invention there is herein provided a combination comprising an anti-BCMA antigen binding protein and a gamma-secretase inhibitor for use in treating cancer or other B-cell mediated disease or disorders.

B-cell disorders can be divided into defects of B-cell development/immunoglobulin production (immunodeficiencies) and excessive/uncontrolled proliferation (lymphomas, leukemias). As used herein, B-cell disorder refers to both types of diseases, and methods are provided for treating B-cell disorders with an antigen binding protein.

Examples of cancers and in particular B-cell mediated or plasma cell mediated diseases or antibody mediated diseases or disorders include Multiple Myeloma (MM), chronic lymphocytic leukemia (CLL), Follicular Lymphoma (FL), Diffuse Large B-Cell Lymphoma (DLBCL), Non-secretory multiple myeloma, Smoldering multiple myeloma, Monoclonal gammopathy of undetermined significance (MGUS), Solitary plasmacytoma (Bone, Extramedullary), Lymphoplasmacytic lymphoma (LPL), Waldenström's Macroglobulinemia, Plasma cell leukemia, Primary Amyloidosis (AL), Heavy chain disease, Systemic lupus erythematosus (SLE), POEMS syndrome/osteosclerotic myeloma, Type I and II cryoglobulinemia, Light chain deposition disease, Goodpasture's syndrome, Idiopathic thrombocytopenic purpura (ITP), Acute glomerulonephritis, Pemphigus and Pemphigoid disorders, and Epidermolysis bullosa acquisita; or any Non-Hodgkin's Lymphoma B-cell leukemia (NHL) and Hodgkin's lymphoma (HL).

In a particular embodiment, the disease or disorder is selected from the group consisting of Multiple Myeloma (MM), Non-Hodgkin's Lymphoma B-cell leukemia (NHL), Follicular Lymphoma (FL), and Diffuse Large B-Cell Lymphoma (DLBCL).

In one embodiment of the present invention the disease is Multiple Myeloma or Non-Hodgkin's Lymphoma B-cell leukemia (NHL).

In one embodiment of the present invention the disease is Multiple Myeloma.

In one embodiment of the invention the cancer may be a hematopoietic (or hematologic or haematological or blood-related) cancer, for example, cancers derived from blood cells or immune cells, which may be referred to as "liquid tumors". In one embodiment the cancer is a B-cell related cancer and particularly a BCMA-expressing cancer. In a further embodiment the cancer is a leukemia such as chronic myelocytic leukemia, acute myelocytic leukemia, chronic lymphocytic leukemia and acute lymphocytic leukemia. In another embodiment the cancer is a lymphoma such as non-Hodgkin's lymphoma, Hodgkin's lymphoma; and the like. In another embodiment the cancer is a plasma cell malignancy such as multiple myeloma, MGUS AL Amyloidosis, and Waldenstrom's macroglobulinemia.

In one embodiment the cancer is multiple myeloma. In another embodiment, the cancer is relapsed and/or refractory multiple myeloma. In another embodiment, the patient with relapsed and/or refractory multiple myeloma has been previously treated with at least one, at least two, at least three or at least four therapeutics to treat the multiple myeloma.

In another embodiment, the patient may have had 0, 1, 2, 3, or 4 or more prior lines of treatment before being treated with the combinations described herein. In another embodiment, the patient may have relapsed and/or refractory multiple myeloma and have had 0, 1, 2, 3, or 4 or more prior lines of treatment before being treated with the combinations described herein. In another embodiment, the patient has been previously treated with at least 3 prior lines that may include the following: an immunomodulatory drug (IMiD), a proteasome inhibitor (PI) and anti-CD38 treatment (e.g., daratumumab). Lines of therapy may be defined by consensus panel of the International Myeloma Workshop (IMWG) [Rajkumar, 2011].

In one aspect of the invention as herein provided the BCMA antigen binding protein is administered at a specific dose or dose range. Throughout, mg/kg refers to milligrams of the therapeutic (e.g., antigen binding protein) per kilogram of patient body weight. In one aspect of the invention as herein provided the BCMA antigen binding protein is administered at a dose of about 0.5-4.0 mg/kg or about 1.0 to 4.0 mg/kg. In one embodiment the anti-BCMA antigen binding protein is administered at a dose of about 0.5 to 2.0 mg/kg, about 0.5 to 1.0 mg/kg about 1.0 to 3.0 mg/kg, or about 2.0 to 4.0 mg/kg or about 2.0 to 3.0 mg/kg. In a further embodiment the anti-BCMA antigen binding protein is administered at a dose of about 0.5 to 2.0 mg/kg or about 2.0 to 3.5 mg/kg. In a further embodiment the anti-BCMA antigen binding protein is administered at a dose of about 0.5 mg/kg, about 0.95 mg/kg, about 1 mg/kg, about 1.25 mg/kg, about 1.7 mg/kg, about 1.9 mg/kg, about 2.5 mg/kg, or about 3.4 mg/kg.

In another embodiment, the therapeutically effective dose of the BCMA antigen binding protein is a fixed dose rather than in mg/kg. Using a fixed dosing could result in a similar range of exposures as that of body weight-based dosing. Fixed dosing may offer the advantage of reduced dosing errors, reduced drug wastage, shorten preparation time, and improve ease of administration. Thus, in one embodiment, the fixed dose of the BCMA antigen binding protein is based on a reference body weight (median participating weight) of 70 kg or 80 kg.

In one aspect of the invention as herein provided the gamma-secretase inhibitor is administered at a dose of about 25-220 mg. In one embodiment the gamma-secretase inhibitor is administered at a dose of about 50-150 mg. In one embodiment the gamma-secretase inhibitor is administered at a dose of about 50 mg, about 100 mg, or about 150 mg. In one embodiment the gamma-secretase inhibitor is administered at a dose of 50 mg, 100 mg, or 150 mg. In one embodiment the gamma-secretase inhibitor is administered at a dose of 50 mg. In one embodiment the gamma-secretase inhibitor is administered at a dose of 100 mg. In one embodiment the gamma-secretase inhibitor is administered at a dose of 150 mg.

In one embodiment the anti-BCMA antigen binding protein is administered at a dose of about 3.4 mg/kg, and the gamma-secretase inhibitor is administered at a dose of about 150 mg.

In one embodiment the anti-BCMA antigen binding protein is administered at a dose of about 2.5 mg/kg, and the gamma-secretase inhibitor is administered at a dose of about 150 mg.

In a further embodiment the anti-BCMA antigen binding protein is administered at a dose of about 1.9 mg/kg, and the gamma-secretase inhibitor is administered at a dose of about 150 mg.

In a further embodiment the anti-BCMA antigen binding protein is administered at a dose of about 0.95 mg/kg, and the gamma-secretase inhibitor is administered at a dose of about 150 mg.

In one embodiment the anti-BCMA antigen binding protein is administered at a dose of about 3.4 mg/kg, and the gamma-secretase inhibitor is administered at a dose of about 100 mg.

In one embodiment the anti-BCMA antigen binding protein is administered at a dose of about 2.5 mg/kg, and the gamma-secretase inhibitor is administered at a dose of about 100 mg.

In a further embodiment the anti-BCMA antigen binding protein is administered at a dose of about 1.9 mg/kg, and the gamma-secretase inhibitor is administered at a dose of about 100 mg.

In a further embodiment the anti-BCMA antigen binding protein is administered at a dose of about 0.95 mg/kg, and the gamma-secretase inhibitor is administered at a dose of about 100 mg.

In one embodiment the anti-BCMA antigen binding protein is administered at a dose of about 3.4 mg/kg, and the gamma-secretase inhibitor is administered at a dose of about 50 mg.

In one embodiment the anti-BCMA antigen binding protein is administered at a dose of about 2.5 mg/kg, and the gamma-secretase inhibitor is administered at a dose of about 50 mg.

In a further embodiment the anti-BCMA antigen binding protein is administered at a dose of about 1.9 mg/kg, and the gamma-secretase inhibitor is administered at a dose of about 50 mg.

In a further embodiment the anti-BCMA antigen binding protein is administered at a dose of about 0.95 mg/kg, and the gamma-secretase inhibitor is administered at a dose of about 50 mg.

In one embodiment the gamma-secretase inhibitor is administered twice daily (BID). In one embodiment the gamma-secretase inhibitor is given every day. In yet another embodiment, the gamma-secretase inhibitor may be given on a “7-day on/14-day off” schedule wherein the gamma-secretase inhibitor is administered twice daily (BID) on days 1-7 of a 21-day cycle and not administered on day 8 through day 14.

In one aspect of the invention the gamma-secretase inhibitor may be administered concurrently or sequentially to the anti-BCMA antigen binding protein. In one embodiment the gamma-secretase inhibitor is administered before the anti-BCMA antigen binding protein. For example, in one aspect the gamma-secretase inhibitor is administered at least 1 hour before the anti-BCMA antigen binding protein.

In one aspect of the invention the anti-BCMA antigen binding protein is dosed weekly. In a further aspect the anti-BCMA antigen binding protein is dosed once every 21 days (i.e., day 1 of a 21-day cycle).

In a further embodiment the dose of the anti-BCMA antigen binding protein is tailored to control maximum plasma concentration, for example, the dose is split and administered, e.g., a week apart. In one embodiment the anti-BCMA antigen binding protein is given at Day 1 (half of the full dose) and Day 8 (half of the full dose) of a 21-day cycle. For example, if the full dose is 3.4 mg/kg a “split dose” regimen may comprise a dose of 1.7 mg/kg of day 1 and another dose of 1.7 mg/kg on day 8 of a 21-day cycle. In another embodiment, if the full dose is 2.5 mg/kg a “split dose” regimen may comprise a dose of 1.25 mg/kg of day 1 and another dose of 1.25 mg/kg on day 8 of a 21-day cycle. In another embodiment, if the full dose is 1.9 mg/kg a “split dose” regimen may comprise a dose of 0.95 mg/kg of day 1 and another dose of 0.95 mg/kg on day 8 of a 21-day cycle.

In one embodiment about 0.95 mg/kg, about 1.9 mg/kg, about 2.5 mg/kg, or about 3.4 mg/kg of an anti-BCMA antigen binding protein is administered on day 1 of a 21-day cycle.

In one embodiment 0.95 mg/kg, 1.9 mg/kg, 2.5 mg/kg, or 3.4 mg/kg of an anti-BCMA antigen binding protein is administered on day 1 of a 21-day cycle. In one embodiment 0.95 mg/kg of an anti-BCMA antigen binding protein is administered on day 1 of a 21-day cycle. In one embodiment 1.9 mg/kg, of an anti-BCMA antigen binding protein is administered on day 1 of a 21-day cycle. In one embodiment 2.5 mg/kg of an anti-BCMA antigen binding protein is administered on day 1 of a 21-day cycle.

In a further embodiment a loading dose of the anti-BCMA antigen binding protein is administered on day 1 of a 21-day cycle followed by a lower dose in subsequent cycles. Any of the dosages contemplated by the invention as provided herein may be administered in this way. For example, dose 1 may comprise about 3.4 mg/kg of the anti-BCMA antigen binding protein being administered, and subsequent cycles may use a dose of about 2.4 mg/kg of the anti-BCMA antigen binding protein.

In one aspect of the invention as herein described the anti-BCMA antigen binding protein is an anti-BCMA antibody or fragment thereof or a CAR-T or an immunoconjugate. In one embodiment the anti-BCMA antigen binding protein is an anti-BCMA antibody. In a further embodiment the anti-BCMA antigen binding protein is a monoclonal antibody. In a further embodiment the anti-BCMA antigen binding protein is humanized.

In one aspect of the invention as herein described the anti-BCMA antigen binding protein comprises CDR sequences which have at least 90% or 95% or 99% sequence identity to CDRH1 according to SEQ ID NO:1; CDRH2 according to SEQ ID NO:2; CDRH3 according to SEQ ID NO:3; CDRL1 according to SEQ ID NO:4; CDRL2 according to SEQ ID NO:5; and CDRL3 according to SEQ ID NO:6.

In one embodiment the anti-BCMA antigen binding protein comprises CDRH1 according to SEQ ID NO:1; CDRH2 according to SEQ ID NO:2; CDRH3 according to SEQ ID NO:3; CDRL1 according to SEQ ID NO:4; CDRL2 according to SEQ ID NO:5; and CDRL3 according to SEQ ID NO:6. In one embodiment the anti-BCMA antigen binding protein comprises a heavy chain variable region (VH) according to SEQ ID NO:7; and a light chain variable region (VL) according to SEQ ID NO:8. In a further embodiment the anti-BCMA antigen binding protein comprises a heavy chain (H) according to SEQ ID NO:9 and a light chain (L) according to SEQ ID NO:10.

In one aspect of the invention as herein described the anti-BCMA antigen binding protein is further conjugated.

In one embodiment, the anti-BCMA antigen binding protein is an immunoconjugate comprising an antigen binding protein according to the invention as herein described including, but not limited to, an antibody conjugated to one or more cytotoxic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate). In a further embodiment the anti-BCMA antigen binding protein is conjugated to a toxin such as an auristatin, e.g., monomethyl auristatin E (MMAE) or monomethyl auristatin F (MMAF). In one embodiment the anti-BCMA antigen binding protein is conjugated to monomethyl auristatin F (MMAF).

In one embodiment, the anti-BCMA antigen binding protein is an immunoconjugate having the following general structure:

ABP-((Linker)n-Ctx)m wherein

ABP is an antigen binding protein

Linker is either absent or any a cleavable or non-cleavable linker

Ctx is any cytotoxic agent described herein n is 0, 1, 2, or 3 and m is 1, 2, 3, 4, 5, 6, 7, 8, 9 or 10.

Exemplary linkers include 6-maleimidocaproyl (MC), maleimidopropanoyl (MP), valine-citrulline (val-cit), alanine-phenylalanine (ala-phe), p-aminobenzyloxycarbonyl (PAB), N-Succinimidyl 4-(2-pyridylthio)pentanoate (SPP), N-succinimidyl 4-(N-maleimidomethyl)cyclohexane-1 carboxylate (SMCC), and N-succinimidyl (4-iodo-acetyl) aminobenzoate (SIAB).

In one embodiment, the anti-BCMA antigen binding protein is an immunoconjugate containing a monoclonal antibody linked to MMAE or MMAF. In another embodiment, the anti-BCMA antigen binding protein is an immunoconjugate containing a monoclonal antibody linked to MMAE or MMAF by an MC linker as depicted in the following structures:

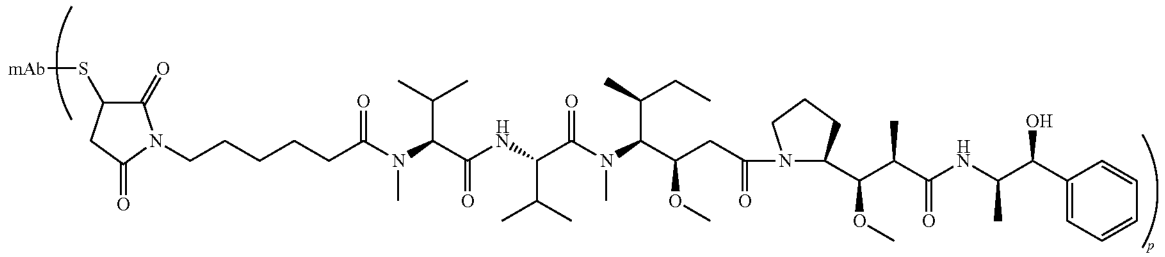

L-MC-MMAE

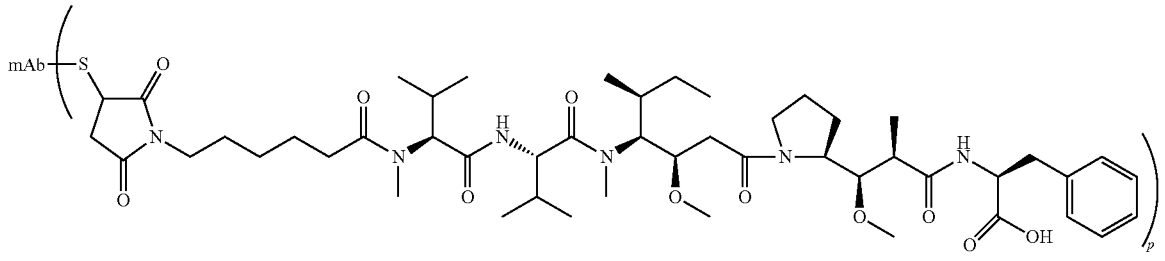

L-MC-MMAF

In one embodiment, the anti-BCMA antigen binding protein is the antibody belantamab. In another embodiment, the anti-BCMA antigen binding protein is the immunoconjugate belantamab mafodotin.

The conjugated antibodies (antibody-drug conjugates or ADCs) of the present invention are powerful anti-cancer agents designed to allow specific targeting of highly potent cytotoxic agents to tumor cells while sparing healthy tissues. Despite the use of tumor-specific antibodies, the emerging clinical data with ADCs indicates that adverse events frequently occur before ADCs have reached their optimal therapeutic dose. As such, despite these ADCs being highly active in preclinical tumor models their therapeutic window in the clinic is narrow and dosing regimens seem hampered by dose-limiting toxicities that could not always be predicted based on data from preclinical models.

Therapies which could be combined to synergistically enhance therapeutic efficacy without worsening the safety profile would be a major advancement in the treatment of cancer patients particularly with regards to the incidence and severity of treatment-emergent adverse events such as ocular toxicity.

Fundamentally, a combination with a drug which could enhance the efficacy of doses leading to overall responses rates (ORR) which are markedly higher whilst having the best benefit-risk profile would lead to a paradigm shift in the management of patients treated with such antigen binding proteins.

The key to achieving the optimal benefit risk profile is dependent on the dosing regimen of the therapies.

In one aspect of the invention as herein described the administration of the anti-BCMA antigen binding protein for example after the gamma-secretase inhibitor at a given time point and controlled dosage allows the opportunity for the plasma concentration to reach its peak and therefore to gain maximum effect from the addition of the anti-BCMA antigen binding protein.

In one aspect of the invention as herein described the gamma-secretase inhibitor is any one of: nirogacestat (PF-03084014); LY3039478 (crenigacestat); CB-103; Tarenflurbil; Semagacestat; RG-4733; EVP-0962; Avagacestat; MK-0752; BMS-906024; or LY450139 (semagacestat).

In one embodiment the gamma-secretase inhibitor is nirogacestat, ((S)-2-(((S)-6,8-difluoro-1,2,3,4-tetrahydronaphthalen-2-yl)amino)-N-(1-(2-methyl-1-(neopentylamino)propan-2-yl)-1H-imidazol-4-yl)pentanamide), (PF-03084014) which has a chemical structure of:

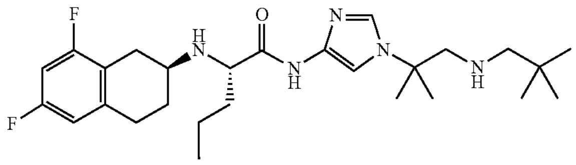 [SMILES: CCC[C@H](N[C@H]1CCc2cc(F)cc(F)c2C1)C(=O)Nc1cn(C(C)(C)CNCC(C)(C)C)cn1]

In one aspect of the present invention there is herein provided a combination comprising an anti-BCMA antigen binding protein and a gamma-secretase inhibitor for use in preventing and/or reducing ocular toxicity in a patient with cancers, such as multiple myeloma. In one embodiment, ocular toxicity is prevented or reduced when compared to a patient treated with the anti-BCMA antigen binding protein alone (monotherapy).

"Prevented" refers to the patient not developing any ocular toxicity signs, diagnoses, or symptoms. "Reduced" refers to any reduction in severity or grade of ocular toxicity signs, diagnoses, or symptoms.

"Ocular toxicity" refers to any unintended exposure of a therapeutic agent to ocular tissue. Ocular toxicity can include: changes in corneal epithelium, dry eyes, irritation, redness, blurred vision, dry eyes, photophobia, and/or changes in visual acuity.

Ophthalmic examination may be conducted by an ophthalmologist or optometrist. An ophthalmic examination may include one or more of the following:

1. Best corrected visual acuity,
2. Documentation of manifest refraction and the method used to obtain best corrected visual acuity,
3. Current glasses prescription (if applicable),
4. Intraocular pressure measurement,
5. Anterior segment (slit lamp) examination including fluorescein staining of the cornea and lens examination, 6. Dilated funduscopic examination, and/or
7. An ocular surface disease index (OSDI) which is visual function questionnaire that assess the impact of potential ocular change in vision on function and health-related quality of life.

The above methods are known and practiced by those skilled in the art. The ophthalmic examination may occur before, during, and/or after treatment.

In one aspect of the invention there is provided a method of treating cancer in a subject in need thereof comprising administering a therapeutically effective dose of an anti-BCMA antigen binding protein and a gamma-secretase inhibitor according to the invention as described herein.

In one aspect of the invention there is provided a method of treating cancer in a subject in need thereof comprising administering:

i) a therapeutically effective dose of an anti-BCMA antigen binding protein comprising CDRH1 according to SEQ ID NO:1; CDRH2 according to SEQ ID NO:2; CDRH3 according to SEQ ID NO:3; CDRL1 according to SEQ ID NO:4; CDRL2 according to SEQ ID NO:5; and CDRL3 according to SEQ ID NO:6; and ii) nirogacestat.

In one aspect of the invention there is provided a method of treating cancer in a subject in need thereof comprising administering:

i) a therapeutically effective dose of an anti-BCMA antigen binding protein comprising a heavy chain variable region (VH) according to SEQ ID NO:7; and a light chain variable region (VL) according to SEQ ID NO:8; and ii) nirogacestat.

In one aspect of the invention there is provided a method of treating cancer in a subject in need thereof comprising administering:

i) a therapeutically effective dose of an anti-BCMA antigen binding protein comprising a heavy chain (H) according to SEQ ID NO:9 and a light chain (L) according to SEQ ID NO:10; and ii) nirogacestat.

In one aspect of the invention there is provided a method of treating cancer in a subject in need thereof comprising administering belantamab mafodotin and nirogacestat.

In one aspect of the invention there is provided a method of treating cancer in a subject in need thereof comprising administering 0.95 mg/kg, 1.9 mg/kg, 2.5 mg/kg, or 3.4 mg/kg belantamab mafodotin and 50 mg, 100 mg, or 150 mg nirogacestat.

In one aspect of the invention there is provided a method of treating cancer in a subject in need thereof comprising administering 0.95 mg/kg, 1.9 mg/kg, 2.5 mg/kg, or 3.4 mg/kg belantamab mafodotin on day 1 of a 21-day cycle and 50 mg, 100 mg, or 150 mg nirogacestat twice daily (BID).

In one aspect of the invention there is provided a method of treating cancer in a subject in need thereof comprising administering 0.95 mg/kg, 1.9 mg/kg, 2.5 mg/kg, or 3.4 mg/kg belantamab mafodotin, wherein half of the dose is administered on day 1 and half of the dose is administered on day 8 of a 21-day cycle; and 50 mg, 100 mg, or 150 mg nirogacestat twice daily (BID) on days 1-7 of a 21-day cycle.

In one aspect of the invention there is provided a method of treating multiple myeloma in a subject in need thereof comprising administering 0.95 mg/kg, 1.9 mg/kg, 2.5 mg/kg, or 3.4 mg/kg belantamab mafodotin on day 1 of a 21-day cycle and 50 mg, 100 mg, or 150 mg nirogacestat twice daily (BID).

In one aspect of the invention there is provided a method of treating multiple myeloma in a subject in need thereof comprising administering 0.95 mg/kg, 1.9 mg/kg, 2.5 mg/kg, or 3.4 mg/kg belantamab mafodotin, wherein half of the dose is administered on day 1 and half of the dose is administered on day 8 of a 21-day cycle; and 50 mg, 100 mg, or 150 mg nirogacestat twice daily (BID) on days 1-7 of a 21-day cycle.

In one aspect there is provided a combination comprising an anti-BCMA antigen binding protein and a gamma-secretase inhibitor according to the invention as described herein for use in the treatment of cancer.

In one aspect there is provided a combination comprising a therapeutically effective dose of an anti-BCMA antigen binding protein comprising CDRH1 according to SEQ ID NO:1; CDRH2 according to SEQ ID NO:2; CDRH3 according to SEQ ID NO:3; CDRL1 according to SEQ ID NO:4; CDRL2 according to SEQ ID NO:5; and CDRL3 according to SEQ ID NO:6; and nirogacestat, for use in the treatment of cancer.

In one aspect there is provided a combination comprising a therapeutically effective dose of an anti-BCMA antigen binding protein comprising heavy chain variable region (VH) according to SEQ ID NO:7; and a light chain variable region (VL) according to SEQ ID NO:8; and nirogacestat, for use in the treatment of cancer.

In one aspect there is provided a combination comprising a therapeutically effective dose of an anti-BCMA antigen binding protein comprising heavy chain (H) according to SEQ ID NO:9 and a light chain (L) according to SEQ ID NO:10; and nirogacestat, for use in the treating cancer.

In one aspect there is provided a combination comprising belantamab mafodotin and nirogacestat for use in the treatment of cancer.

In one aspect there is provided a combination comprising belantamab mafodotin and nirogacestat for use in the treatment of cancer, wherein belantamab mafodotin is administered at 0.95 mg/kg, 1.9 mg/kg, 2.5 mg/kg, or 3.4 mg/kg and nirogacestat is administered at 50 mg, 100 mg, or 150 mg.

In one aspect there is provided a combination comprising belantamab mafodotin and nirogacestat for use in the treatment of cancer, wherein belantamab mafodotin is administered at 0.95 mg/kg, 1.9 mg/kg, 2.5 mg/kg, or 3.4 mg/kg on day 1 of a 21-day cycle and nirogacestat is administered at 50 mg, 100 mg, or 150 mg twice daily (BID).

In one aspect there is provided a combination comprising belantamab mafodotin and nirogacestat for use in the treatment of cancer, wherein belantamab mafodotin is administered at 0.95 mg/kg, 1.9 mg/kg, 2.5 mg/kg, or 3.4 mg/kg and half of the dose is administered on day 1 and half of the dose is administered on day 8 of a 21-day cycle; and nirogacestat is administered at 50 mg, 100 mg, or 150 mg twice daily (BID) on days 1-7 of a 21-day cycle.

In one aspect there is provided a combination comprising belantamab mafodotin and nirogacestat for use in the treatment of multiple myeloma, wherein belantamab mafodotin is administered at 0.95 mg/kg, 1.9 mg/kg, 2.5 mg/kg, or 3.4 mg/kg and nirogacestat is administered at 50 mg, 100 mg, or 150 mg.

In one aspect there is provided a combination comprising belantamab mafodotin and nirogacestat for use in the treatment of multiple myeloma, wherein belantamab mafodotin is administered at 0.95 mg/kg, 1.9 mg/kg, 2.5 mg/kg, or 3.4 mg/kg and half of the dose is administered on day 1 and half of the dose is administered on day 8 of a 21-day cycle; and nirogacestat is administered at 50 mg, 100 mg, or 150 mg twice daily (BID) on days 1-7 of a 21-day cycle.

In one aspect there is provided a combination for use in the manufacture of a medicament for treating cancer wherein the combination comprises an anti-BCMA antigen binding protein and a gamma-secretase inhibitor, according to the invention as described herein.

In one aspect there is provided a kit for use in treating cancer comprising:

(i) an anti-BCMA antigen binding protein according to the invention as described herein; and, (ii) instructions for use when combined with a gamma-secretase inhibitor according to the invention as described herein.

In one aspect there is provided a kit for use in treating cancer comprising:

(i) a gamma-secretase inhibitor according to the invention as described herein; and, (ii) instructions for use when combined with an anti-BCMA antigen binding protein according to the invention as described herein.

In one aspect there is provided a kit for use in treating cancer comprising:

(i) an anti-BCMA antigen binding protein according to the invention as described herein;

(ii) a gamma-secretase inhibitor according to the invention as described herein; and, (iii) instructions for use.

In one aspect of the invention there is provided a method of preventing ocular toxicity in a patient with cancer, such as multiple myeloma, comprising administering a therapeutically effective dose of an anti-BCMA antigen binding protein and a gamma-secretase inhibitor.

In one aspect of the invention there is provided a method of reducing ocular toxicity in a patient with cancer, such as multiple myeloma, comprising administering a therapeutically effective dose of an anti-BCMA antigen binding protein and a gamma-secretase inhibitor.

DEFINITIONS

The term "combination" described herein refers to at least two therapeutic agents. As used herein the term "therapeutic agent" is understood to mean a substance that produces a desired effect in a tissue, system, animal, mammal, human, or other subject. In one embodiment, the combination can contain an additional therapeutic agent, such as, for example, an additional cancer therapeutic agent. In one embodiment the additional cancer therapeutic is an immunomodulatory imide drug (IMiD) such as thalidomide, lenalidomide, pomalidomide, apremilast, or other thalidomide analogs.

The administration of the combinations of the invention may be advantageous over the individual therapeutic agents in that the combinations may provide one or more of the following improved properties when compared to the individual administration of a single therapeutic agent alone: i) a greater anticancer effect than the most active single agent, ii) synergistic or highly synergistic anticancer activity, iii) a dosing protocol that provides enhanced anticancer activity with reduced side effect profile, iv) a reduction in the toxic effect profile, v) an increase in the therapeutic window, or vi) an increase in the bioavailability of one or both of the therapeutic agents.

The combinations described herein can be in the form of a pharmaceutical composition. A "pharmaceutical composition" contains a combination described herein, and one or more pharmaceutically acceptable carriers, diluents, or excipients. The carrier(s), diluent(s) or excipient(s) must be acceptable in the sense of being compatible with the other ingredients of the formulation, capable of pharmaceutical formulation, and not deleterious to the recipient thereof. In one embodiment, each therapeutic agent in a combination is individually formulated into its own pharmaceutical composition and each of the pharmaceutical compositions are administered to treat cancer. In this embodiment, each of the pharmaceutical compositions may have the same or different carriers, diluents or excipients.

The anti-BCMA antigen binding proteins in the combinations described herein are useful in the treatment or prevention of cancers. The anti-BCMA antigen binding proteins described herein may bind to human BCMA, including, for example, human BCMA containing the amino acid sequence of GenBank Accession Number Q02223.2, or genes encoding human BCMA having at least 90 percent homology or at least 90 percent identity thereto.

The term "antigen binding protein" as used herein refers to antibodies, antibody fragments and other protein constructs which are capable of binding to human BCMA. The antigen binding proteins of the present invention may comprise heavy chain variable regions and light chain variable regions of the invention which may be formatted into the structure of a natural antibody or functional fragment or equivalent thereof. An antigen binding protein of the invention may therefore comprise the VH regions of the invention formatted into a full-length antibody, a $(Fab')^2$ fragment, a Fab fragment, or equivalent thereof (such as scFV, bi- tri- or tetra-bodies, Tandabs etc.), when paired with an appropriate light chain. The antibody may be an IgG1, IgG2, IgG3, or IgG4; or IgM; IgA, IgE or IgD; or a modified variant thereof. The constant domain of the antibody heavy chain may be selected accordingly. The light chain constant domain may be a kappa or lambda constant domain. Furthermore, the antigen binding protein may comprise modifications of all classes e.g. IgG dimers, Fc mutants that no longer bind Fc receptors or mediate C1q binding. The antigen binding protein may also be a chimeric antibody of the type described in WO86/01533 which comprises an antigen binding region and a non-immunoglobulin region.

In another aspect the antigen binding protein is selected from the group consisting of a dAb, Fab, Fab', $F(ab')_2$, Fv, diabody, triabody, tetrabody, miniantibody, and a minibody. In one aspect of the present invention the antigen binding protein is a humanized or chimaeric antibody. In a further aspect the antibody is humanized. In one aspect the antibody is a monoclonal antibody. Chimeric antigen receptors (CARs) have been developed as artificial T cell receptors to generate novel specificities in T cells without the need to bind to MHC-antigenic peptide complexes. These synthetic receptors contain a target binding domain that is associated with one or more signalling domains via a flexible linker in a single fusion molecule. The target binding domain is used to target the T cell to specific targets on the surface of pathologic cells and the signalling domains contain molecular machinery for T cell activation and proliferation. The flexible linker which passes through the T cell membrane (i.e. forming a transmembrane domain) allows for cell membrane display of the target binding domain of the CAR. CARs have successfully allowed T cells to be redirected against antigens expressed at the surface of tumor cells from various malignancies including lymphomas and solid tumors (Jena et al. (2010) Blood, 116(7):1035-44).

In one embodiment, the anti-BCMA antigen binding protein is an antibody which has enhanced antibody dependent cell mediated cytotoxic activity (ADCC) effector function. The term "Effector Function" as used herein is meant to refer to one or more of Antibody dependent cell mediated cytotoxic activity (ADCC), Complement-dependent cytotoxic activity (CDC) mediated responses, Fc-mediated phagocytosis and antibody recycling via the FcRn receptor. "Gamma-secretase" is a multi-subunit integral membrane protease complex which cleaves single pass transmembrane proteins within the transmembrane domain. The gamma-secretase complex plays a role in a processing of a variety of substrates, including Notch, CD44, Cadherins, and ephrin B2, as well as cleaving amyloid precursor protein into amyloid beta peptide that is implicated in Alzheimer's disease. The gamma-secretase complex is also known to cleave B-cell maturation antigen (BCMA). Exemplary gamma-secretase inhibitors (GSIs) include small molecules, peptidomimetic compounds or gamma-secretase-specific binding proteins. A GSI can target any one or more of the gamma-secretase complex proteins provided that the gamma-secretase cleavage activity is reduced compared to uninhibited gamma-secretase. In certain embodiments, the gamma-secretase activity is reduced at least about 80%. Assays for measuring gamma-secretase activity are known in the art (see, e.g., Laurent et al., 2015). For example, the level of soluble BCMA can be a surrogate measure for gamma-secretase activity. The gamma-secretase inhibitor nirogacestat has a rapid absorption with a median time of occurrence of Cmax (Tmax) values of 1 to 2.5 hour. Nirogacestat is eliminated slowly with a terminal half-life ranging from 22.6 to 38.6 hours in oncology patients. Nirogacestat exposure increases generally in a dose-proportional fashion between 20 and 330 mg BID (twice daily dosing). Following repeated BID administration, steady-state is achieved by day 8 and the median accumulation ratio ranged from 1.18 to 2.84

"CDRs" are defined as the complementarity determining region amino acid sequences of an antigen binding protein. These are the hypervariable regions of immunoglobulin heavy and light chains. There are three heavy chain and three light chain CDRs (or CDR regions) in the variable portion of an immunoglobulin. Thus, "CDRs" as used herein refers to all three heavy chain CDRs, all three light chain CDRs, all heavy and light chain CDRs, or at least two CDRs. The terms "VH" and "VL" are used herein to refer to the heavy chain variable region and light chain variable region respectively of an antigen binding protein.

Throughout this specification, amino acid residues in variable domain sequences and full length antibody sequences are numbered according to the Kabat numbering convention. Similarly, the terms "CDR", "CDRL1", "CDRL2", "CDRL3", "CDRH1", "CDRH2", "CDRH3" used in the Examples follow the Kabat numbering convention (see Kabat et al., Sequences of Proteins of Immunological Interest, 5th Ed., U.S. Department of Health and Human Services, National Institutes of Health (1991)). There are alternative numbering conventions for CDR sequences, for example those set out in Chothia et al. (1989) Nature 342: 877-883. Other numbering conventions for CDR sequences are also available to a skilled person including "AbM" (University of Bath) and "contact" (University College London) methods.

SEQUENCE LISTING

SEQ. ID. NO. 1-CDRH1
NYWMH

SEQ. ID. NO. 2: CDRH2
ATYRGHSDTYYNQKFKG

-continued

SEQUENCE LISTING

SEQ. ID. NO. 3: CDRH3
GAIYDGYDVLDN

SEQ. ID. NO. 4: CDRL1
SASQDISNYLN

SEQ. ID. NO. 5: CDRL2
YTSNLHS

SEQ. ID. NO. 6: CDRL3
QQYRKLPWT

SEQ. ID. NO. 7: heavy chain variable region
QVQLVQSGAEVKKPGSSVKVSCKASGGTFSNYWMHWVRQAPGQGLEWMGA
TYRGHSDTYYNQKFKGRVTITADKSTSTAYMELSSLRSEDTAVYYCARGA
IYDGYDVLDNWGQGTLVTVSS SED. ID. NO. 8: light chain variable region
DIQMTQSPSSLSASVGDRVTITCSASQDISNYLNWYQQKPGKAPKLLIYY
TSNLHSGVPSRFSGSGSGTDFTLTISSLQPEDFATYYCQQYRKLPWTFGQ
GTKLEIKR SEQ. ID. NO. 9: heavy chain region
QVQLVQSGAEVKKPGSSVKVSCKASGGTFSNYWMHWVRQAPGQGLEWMGA
TYRGHSDTYYNQKFKGRVTITADKSTSTAYMELSSLRSEDTAVYYCARGA
IYDGYDVLDNWGQGTLVTVSSASTKGPSVFPLAPSSKSTSGGTAALGCLV
KDYFPEPVTVSWNSGALTSGVHTFPAVLQSSGLYSLSSVVTVPSSSLGTQ
TYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPG
K SEQ. ID. NO. 10: light chain region
DIQMTQSPSSLSASVGDRVTITCSASQDISNYLNWYQQKPGKAPKLLIYY
TSNLHSGVPSRFSGSGSGTDFTLTISSLQPEDFATYYCQQYRKLPWTFGQ
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC

EXAMPLES

Rationale for Combination

Gamma-secretase is an integral membrane protein complex with protease activity against single-pass transmembrane proteins within the transmembrane domain (Wolfe, 2010). One of the substrates for gamma-secretase is BCMA, the target for belantamab mafodotin and belantamab. BCMA is unusual among substrates for gamma-secretase in that it does not require additional proteolytic steps either before or after gamma-secretase cleavage for release of the extracellular domain of BCMA. This cleavage results in a soluble form of BCMA ("sBCMA"). Gamma-secretase is the sole enzyme responsible for production of sBCMA, and inhibition of gamma-secretase reduces sBCMA and increases cell surface levels of BCMA on plasma cells, both in vitro and in vivo. In the context of multiple myeloma, the levels of sBCMA are elevated in multiple myeloma patients and correlated with the percentage of plasma cells in the bone marrow (Sanchez, 2018). In addition, sBCMA has been linked to immunodeficiency seen in patients with multiple myeloma.

Gamma-secretase inhibition would potentially enhance the mechanisms of action of belantamab mafodotin and belantamab through increased cell surface expression and enhanced internalization of BCMA by multiple myeloma cells. Increased cell surface expression of BCMA would increase the amount of belantamab mafodotin and belantamab bound to the cell surface, potentially enhancing the ADCC mechanism of belantamab mafodotin and belantamab through increased FcγR interaction and immune cell recruitment. In addition, blocking shedding of BCMA would potentially increase the internalization of bound belantamab mafodotin and belantamab, allowing enhanced delivery of the cys-mcMMAF toxin to multiple myeloma cells.

In preclinical experiments, using a panel of multiple myeloma and lymphoma cell lines with varying levels of BCMA expression, broad synergy was observed with combination treatment of nirogacestat and belantamab mafodotin and belantamab, in assays designed to measure ADC and ADCC activity.

Example 1

In the example shown in FIG. 1, the multiple myeloma cell line L363 was pre-treated with four different concentrations of nirogacestat (PF-03084014) for 24 hours, then treated with a dose range of belantamab mafodotin or controls for an additional 72 hours and cell viability was measured. Belantamab, nirogacestat alone, conjugated isotype antibody (IgG-MMAF) or the combination of IgG-MMAF and nirogacestat had no effect on cell viability. However, a maximum 1000-fold shift in EC50 was observed with the combination of nirogacestat and belantamab mafodotin compared to belantamab.

Example 2

In the example shown in FIG. 2, ADCC activity of belantamab mafodotin in combination with nirogacestat was evaluated. L363 cells were pre-treated with different concentrations of nirogacestat for 24 hours, exposed to belantamab and FcγR engagement was evaluated with an engineered Jurkat cell line. The EC50 for FcγR engagement was enhanced 10-fold by the combination of nirogacestat and belantamab, over belantamab alone. Similar log-fold shifts were observed with the combination of nirogacestat and belantamab mafodotin in 19 additional multiple myeloma and lymphoma cell lines with evidence of belantamab mafodotin activity. Therefore, preclinical data support the mechanistic rationale for enhancing belantamab mafodotin activity through gamma-secretase inhibition.

Although similar results with other gamma-secretase inhibitors was observed nirogacestat seems to have a better safety profile than other gamma-secretase inhibitors which have been evaluated. An improved safety profile may enable daily dosing of nirogacestat in contrast to many other GSIs. In addition, daily dosing or nirogacestat may improve target coverage by continually preventing BCMA cleavage due to more consistent exposure of the drug. Specifically, the incidence of dose-limiting diarrhea and elevated liver enzymes does not appear to be as high when compared with other gamma-secretase inhibitors, such as RO4929097 or MK-0752 (Messersmith, 2015). Furthermore, unlike other gamma-secretase inhibitors (e.g., semagacestat), there does not seem to be an increased incidence of either secondary primary malignancies (SPM) or treatment-emergent infections with nirogacestat treatment (Messersmith, 2015) (Henley, 2014). Since gamma-secretase inhibitors are pharmacologically and functionally diverse (Ran, 2017), these contrasting findings between different gamma-secretase inhibitors might be related to differences in target binding affinity and drug penetration into specific organ stem cell compartments.

Example 3

In this prophetic example, the synergistic activity of belantamab mafodotin and nirogacestat will be studied in the clinic:

Group 1: Two doses of belantamab mafodotin (i.e., 1.9 mg/kg & 2.5 mg/kg) will be evaluated in up to five separate dosing cohorts in combination with up to three different doses of nirogacestat administered on a continuous BID schedule.

The primary objective of Group 1 is to obtain confirmatory evidence that belantamab mafodotin dose of 1.9 mg/kg when in combination with 50 mg, 100 mg or 150 mg BID nirogacestat has at least a similar Overall Response Rate ("ORR") to the dose of belantamab mafodotin monotherapy used in the common control arm.

The $2^{nd}$ and $3^{rd}$ dosing cohorts in Group 1 can only be initiated in parallel provided the safety profile at the starting doses of belantamab mafodotin (1.9 mg/kg) and nirogacestat (100 mg BID) are determined to be acceptable.

Where the overall safety profile of the starting doses (cohort 1) is determined to be unfavorable, nirogacestat will be reduced to 50 mg BID and the dose of belantamab mafodotin will be unchanged at 1.9 mg/kg (i.e. dose cohort-1). No further reductions in nirogacestat dose intensity to <50 mg BID are permissible as the pharmacodynamic activity (i.e. γ-secretase inhibition) of the drug at such dose levels is thought to be low.

If the 2.5 mg/kg dose of belantamab mafodotin is determined to have an unacceptable safety profile when administered as a single infusion, an option to initiate a "mezzanine" dose level of 2.5 mg/kg administered as two equally divided doses of 1.25 mg/kg on day 1 & day 8 of a Q3W schedule as this dosing schedule would provide ~25% reduction in the maximum concentration while maintaining the same exposure (AUC) over a cycle compared to the Q3W dosing, potentially positively impacting the benefit/risk of belantamab mafodotin.

The maximum evaluable doses in Group 1 are 2.5 mg/kg belantamab mafodotin and 150 mg BID nirogacestat (cohort 4). Cohort 4 will be initiated only if the overall safety profile of cohort 3 (i.e. 2.5 mg/kg belantamab mafodotin & 100 mg BID nirogacestat) is determined to be acceptable. For the avoidance of doubt the acronym BID refers to twice daily dosing.

Group 1 Dosing Levels

Second and Third Dosing Levels can be started simultaneously

| Dose Level | belantamab mafodotin IV Q3 weeks | nirogacestat |
|---|---|---|
| 4 | 2.5 mg/kg | 150 mg |
| 3 | 2.5 mg/kg | 100 mg |
| 2 | 1.9 mg/kg | 150 mg |
| 1 (starting doses) | 1.9 mg/kg | 100 mg |
| −1 | 1.9 mg/kg | 50 mg |

Group 2: This is an optional group which will only be initiated if the primary objective of Group 1 (as described above) has been fulfilled, and if the overall benefit-risk profile of 1.9 mg/kg belantamab mafodotin in combination with 50 mg, 100 mg or 150 mg BID nirogacestat is determined to be acceptable.

The main objective of Group 2 is to identify a single dose of belantamab mafodotin<1.9 mg/kg which when in combination with 50 mg, 100 mg or 150 mg BID nirogacestat has a higher ORR than the belantamab mafodotin monotherapy dose in the common control arm.

One or more separate dosing cohorts at belantamab mafodotin dose levels<1.9 mg/kg can be evaluated in Group 2 in combination with one specific dose of nirogacestat. These lower belantamab mafodotin dose levels will be selected for evaluation on the basis of pharmacokinetics ("PK"), Treatment Emergent Adverse Events ("TEAE") and ORR findings.

Group 3: This is an optional group which will only be initiated if 3.4 mg/kg is belantamab mafodotin monotherapy dose in the common control arm, and the safety/tolerability of 2.5 mg/kg belantamab mafodotin administered as a single infusion on day 1, or as two equally divided doses on day 1 and day 8, is favorable.

The main objective of Group 3 is to demonstrate that the 3.4 mg/kg dose of belantamab mafodotin when administered as two equally divided doses of 1.7 mg/kg on day 1 & day 8 (to attenuate risk of potentially Cmax driven toxicities) when in combination with one specific dose of nirogacestat has a higher ORR than the common control arm, but with an overall safety profile which is not markedly worse than 3.4 mg/kg belantamab mafodotin monotherapy within the platform trial.

If potentially overlapping nirogacestat-related grade 3 toxicities arise more than 7 days after treatment initiation, it may be possible to administer nirogacestat on a "7-days on/14-days off" twice a day dosing schedule, especially since pharmacodynamically active plasma levels of nirogacestat are attained rapidly, typically <48 hours after treatment initiation, and steady-state plasma levels of nirogacestat are attained by day 8 with a twice a day dosing schedule.

Example 4

A lower starting dose of belantamab mafodotin of 0.95 mg/kg has been selected for this prophetic sub-study. The clinical activity of belantamab mafodotin monotherapy doses<1.9 mg/kg is predicted to be low based on Bayesian logistic regression modelling (BLRM) of the FTIH trial data, although a small number of participants were treated at doses lower than 1.9 mg/kg (e.g. n=3 at 0.48 mg/kg, n=4 at 0.96 mg/kg). While the starting dose of 0.95 mg/kg is expected to only have limited efficacy on its own, it is anticipated that nirogacestat will potentiate the effect of belantamab mafodotin. This lower starting dose is anticipated to have an improved safety profile compared to the higher doses used in belantamab mafodotin monotherapy trials, for example corneal toxicity events are likely to be associated with a lower rate of grade 2 events compared to higher doses of 2.5 mg/kg and 3.4 mg/kg, which are associated with higher predicted levels of hematologic response.

Three cohorts will be given 0.95 mg/kg belantamab mafodotin, but with different doses of nirogacestat:

0.95 mg/kg belantamab mafodotin in combination with nirogacestat 50 mg BID 0.95 mg/kg belantamab mafodotin in combination with nirogacestat 100 mg BID 0.95 mg/kg belantamab mafodotin in combination with nirogacestat 150 mg BID.

Nirogacestat will be administered intermittently, e.g., at 7 days-on/14 days-off or continuously. The results from the clinical trials will provide the data to support the optimal dosage regimen required for maximum risk-benefit.

Example 5: ADC Activity

To determine if belantamab mafodotin shows combination synergy with GSIs in an antibody-dependent cytotoxicity assay, multiple myeloma and lymphoma cancer cell lines expressing BCMA were tested in a 3-day cell proliferation assay. After plating cells in 384-well plates, nirogacestat was dosed at the fixed concentrations of 2.5 uM, 0.25 uM, 0.025 uM, and 0.0025 uM. Plates were incubated overnight and then dosed with a 10-point dose titration of belantamab mafodotin from 9.9 ug/ml to 0.00025 ug/ml for each fixed concentration of nirogacestat. After 3-days of incubation, cell viability was analysed using Promega's Cell-titer Glo and analysed using Graphpad software. Representative data is shown in FIG. 3. The results show up to a 3 log-fold shift in potency with belantamab mafodotin in combination with nirogacestat.

Example 6: ADCC Activity

ADCC activity of belantamab, the MMAF-unconjugated form of belantamab mafodotin, was assessed in combination with nirogacestat using Promega's Jurkat ADCC assay. Multiple myeloma and lymphoma cancer cell lines expressing BCMA were plated in a 1536-well format at a ratio of 10:1 (Jurkat effector cells: cancer cells). Immediately afterwards, cells were dosed with nirogacestat at fixed concentrations of 2.5 μM, 0.25 μM, 0.025 μM, and 0.0025 μM. Belantamab was then titrated across each fixed concentration from 9.9 μg/ml to 0.00025 μg/ml. Plates were incubated for 24 hours and assessed for ADCC activity by adding Promega Bio-glo. Data was analyzed using Graphpad software. Representative data for ADCC activity is shown in FIG. 4.

Example 7: sBCMA Levels

Soluble BCMA was detected in 3-day old cell culture supernatant of BCMA-expressing cell lines following treatment with nirogacestat at fixed concentrations of 2.5 μM, 0.25 μM, 0.025 μM, and 0.0025 μM using R&D human sBCMA Elisa kit. We detect a loss of sBCMA in a dose-dependent manner following treatment with nirogacestat (FIG. 5).

Example 8: Cell Surface Detection of BCMA Levels

BCMA cell surface levels were examined by flow cytometry following 3-day old treatment with nirogacestat at fixed concentrations of 2.5 μM, 0.25 μM, 0.025 μM, and 0.0025 μM in BCMA-expressing cell lines. Levels of BCMA were compared to isotype control. An increase in cell surface BCMA was detected in a dose-dependent manner. Representative data of cell surface BCMA levels is shown in FIG. 6.

The invention claimed is:

1. A method of treating a BCMA-expressing cancer in a subject in need thereof, the method comprising administering to the subject:
   i) a therapeutically effective dose of belantamab mafodotin; and
   ii) nirogacestat.

2. The method of claim 1, wherein the belantamab mafodotin is administered to the subject at a dose of at least about 0.95 mg/kg, 1.9 mg/kg, 2.5 mg/kg or 3.4 mg/kg.

3. The method of claim 2, wherein the nirogacestat is administered to the subject at a dose of at least about 50 mg, 100 mg, 150 mg or 200 mg.

4. The method of claim 3, wherein the belantamab mafodotin is administered on day 1 of a 21-day cycle and nirogacestat is administered twice daily (BID).

5. The method of claim 3, wherein a first half of a dose of belantamab mafodotin is administered on day 1 and a second half of a dose of belantamab mafodotin is administered on day 8 of a 21-day cycle; and wherein nirogacestat is administered twice daily (BID) on days 1-7 of a 21-day cycle.

6. The method of claim 1, wherein the cancer is multiple myeloma.

7. The method of claim 1, wherein the BCMA-expressing cancer is relapsed and/or refractory multiple myeloma.

8. The method of claim 7, wherein the subject has received at least one prior line of cancer treatment.

9. The method of claim 8, wherein the subject has received at least 3 prior lines of cancer treatment including an immunomodulatory drug (IMiD), a proteasome inhibitor (PI), and anti-CD38 treatment.

10. The method of claim 6, wherein the administering reduces ocular toxicity in the subject as compared to the administration of a therapeutically effective dose of belantamab mafodotin alone for treatment of the multiple myeloma.

11. The method of claim 10, wherein the ocular toxicity is at least one of: changes in corneal epithelium, dry eyes, irritation, redness, blurred vision, dry eyes, photophobia, or changes in visual acuity.

12. The method of claim 11, wherein the ocular toxicity is measured by at least one of the following methods: best corrected visual acuity, documentation of manifest refraction and the method used to obtain best corrected visual acuity, current glasses prescription (if applicable), intraocular pressure measurement, anterior segment (slit lamp) examination including fluorescein staining of the cornea and lens examination, dilated funduscopic examination, or an ocular surface disease index (OSDI).

13. A combination comprising belantamab mafodotin and a nirogacestat.

14. The combination of claim 13, wherein the combination comprises at least about 0.95 mg/kg, 1.9 mg/kg, 2.5 mg/kg or 3.4 mg/kg belantamab mafodotin.

15. The composition of claim 14, wherein the combination comprises at least about 50 mg, 100 mg, 150 mg, or 200 mg nirogacestat.

16. The method of claim 1, wherein the BCMA-expressing cancer is selected from leukemia and lymphoma.

17. The method of claim 1, wherein the BCMA-expressing cancer is selected from chronic myelocytic leukemia, acute myelocytic leukemia, chronic lymphocytic leukemia, acute lymphocytic leukemia, non-Hodgkin's lymphoma, and Hodgkin's lymphoma.

* * * * *

SEQUENCE LISTING

```
<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<223> OTHER INFORMATION: Artificially Synthesized Sequence

<400> SEQUENCE: 1

Asn Tyr Trp Met His
1               5


<210> SEQ ID NO 2
<211> LENGTH: 17
<212> TYPE: PRT
<213> ORGANISM: Artificial Sequence
<220> FEATURE:
<223> OTHER INFORMATION: Artificially Synthesized Sequence

<400> SEQUENCE: 2

Ala Thr Tyr Arg Gly His Ser Asp Thr Tyr Tyr Asn Gln Lys Phe Lys
1               5                   10                  15

Gly


<210> SEQ ID NO 3
<211> LENGTH: 12
<212> TYPE: PRT
<213> ORGANISM: Artificial Sequence
<220> FEATURE:
<223> OTHER INFORMATION: Artificially Synthesized Sequence

<400> SEQUENCE: 3

Gly Ala Ile Tyr Asp Gly Tyr Asp Val Leu Asp Asn
1               5                   10


<210> SEQ ID NO 4
<211> LENGTH: 11
<212> TYPE: PRT
<213> ORGANISM: Artificial Sequence
<220> FEATURE:
<223> OTHER INFORMATION: Artificially Synthesized Sequence

<400> SEQUENCE: 4

Ser Ala Ser Gln Asp Ile Ser Asn Tyr Leu Asn
1               5                   10


<210> SEQ ID NO 5
<211> LENGTH: 7
<212> TYPE: PRT
<213> ORGANISM: Artificial Sequence
<220> FEATURE:
<223> OTHER INFORMATION: Artificially Synthesized Sequence

<400> SEQUENCE: 5

Tyr Thr Ser Asn Leu His Ser
1               5


<210> SEQ ID NO 6
<211> LENGTH: 9
<212> TYPE: PRT
<213> ORGANISM: Artificial Sequence
<220> FEATURE:
<223> OTHER INFORMATION: Artificially Synthesized Sequence

<400> SEQUENCE: 6
```

-continued

Gln Gln Tyr Arg Lys Leu Pro Trp Thr
1 5

<210> SEQ ID NO 7
<211> LENGTH: 121
<212> TYPE: PRT
<213> ORGANISM: Artificial Sequence
<220> FEATURE:
<223> OTHER INFORMATION: Artificially Synthesized Sequence

<400> SEQUENCE: 7

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Asn Tyr
20 25 30

Trp Met His Trp Val Arg Gln Ala Pro Gly Gln Gly Leu Glu Trp Met
35 40 45

Gly Ala Thr Tyr Arg Gly His Ser Asp Thr Tyr Tyr Asn Gln Lys Phe
50 55 60

Lys Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Gly Ala Ile Tyr Asp Gly Tyr Asp Val Leu Asp Asn Trp Gly
100 105 110

Gln Gly Thr Leu Val Thr Val Ser Ser
115 120

<210> SEQ ID NO 8
<211> LENGTH: 108
<212> TYPE: PRT
<213> ORGANISM: Artificial Sequence
<220> FEATURE:
<223> OTHER INFORMATION: Artificially Synthesized Sequence

<400> SEQUENCE: 8

Asp Ile Gln Met Thr Gln Ser Pro Ser Ser Leu Ser Ala Ser Val Gly
1 5 10 15

Asp Arg Val Thr Ile Thr Cys Ser Ala Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Tyr Thr Ser Asn Leu His Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Arg Lys Leu Pro Trp
85 90 95

Thr Phe Gly Gln Gly Thr Lys Leu Glu Ile Lys Arg
100 105

<210> SEQ ID NO 9
<211> LENGTH: 451
<212> TYPE: PRT
<213> ORGANISM: Artificial Sequence
<220> FEATURE:
<223> OTHER INFORMATION: Artificially Synthesized Sequence

<400> SEQUENCE: 9

Gln Val Gln Leu Val Gln Ser Gly Ala Glu Val Lys Lys Pro Gly Ser

-continued

```
1               5                   10                  15

Ser Val Lys Val Ser Cys Lys Ala Ser Gly Gly Thr Phe Ser Asn Tyr
            20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ile Tyr Asp Gly Tyr Asp Val Leu Asp Asn Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430
```

-continued

```
His Glu Ala Leu His Asn His Tyr Thr Gln Lys Ser Leu Ser Leu Ser
        435                 440                 445

Pro Gly Lys
    450


<210> SEQ ID NO 10
<211> LENGTH: 214
<212> TYPE: PRT
<213> ORGANISM: Artificial Sequence
<220> FEATURE:
<223> OTHER INFORMATION: Artificially Synthesized Sequence

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Arg Lys Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```